(12) United States Patent
Bluechel (10) Patent No.: US 8,142,434 B2
(45) Date of Patent: Mar. 27, 2012

(54) CAM-LOCKING OF CABLE FOR FRACTURE PLATE

(75) Inventor: Tobias Bluechel, Selzach (CH)

(73) Assignee: Stryker Trauma GmbH (DE)

( * ) Notice: Subject to any disclaimer, the term of this patent is extended or adjusted under 35 U.S.C. 154(b) by 338 days.

(21) Appl. No.: 11/975,145

(22) Filed: Oct. 17, 2007

(65) Prior Publication Data

US 2009/0105717 A1   Apr. 23, 2009

(51) Int. Cl.
*A61B 17/56* (2006.01)
*A61B 17/58* (2006.01)
*A61B 17/80* (2006.01)

(52) U.S. Cl. ............................... 606/74; 606/70; 606/280

(58) Field of Classification Search .............. 606/70–71, 606/103, 263, 273, 277–278, 280–299, 74
See application file for complete search history.

(56) References Cited

U.S. PATENT DOCUMENTS

| | | | | |
|---|---|---|---|---|
| 1,159,863 A | * | 11/1915 | Park | 24/134 P |
| 2,226,393 A | * | 12/1940 | Seeger | 24/134 P |
| 2,292,746 A | * | 8/1942 | Donald | 24/134 P |
| 3,080,867 A | | 3/1963 | Eichinger | |
| 3,644,966 A | * | 2/1972 | Higgins | 24/134 P |
| 5,070,805 A | * | 12/1991 | Plante | 114/218 |
| 5,190,545 A | | 3/1993 | Corsi et al. | |
| 5,356,412 A | * | 10/1994 | Golds et al. | 606/74 |
| 5,383,905 A | | 1/1995 | Golds et al. | |
| 5,415,658 A | * | 5/1995 | Kilpela et al. | 606/300 |
| 5,423,820 A | | 6/1995 | Miller et al. | |
| 5,569,253 A | | 10/1996 | Farris et al. | |
| 5,607,429 A | | 3/1997 | Hayano et al. | |
| 5,607,430 A | | 3/1997 | Bailey | |
| 5,649,927 A | | 7/1997 | Kilpela et al. | |
| 5,653,711 A | | 8/1997 | Hayano et al. | |
| 5,665,088 A | * | 9/1997 | Gil et al. | 606/74 |
| 5,665,089 A | | 9/1997 | Dall et al. | |
| 5,702,399 A | * | 12/1997 | Kilpela et al. | 606/308 |

(Continued)

FOREIGN PATENT DOCUMENTS

DE          8203609 U       6/1982

(Continued)

OTHER PUBLICATIONS

Stryker, Dall-Miles Cable System, 2004.

(Continued)

*Primary Examiner* — Thomas C. Barrett
*Assistant Examiner* — Matthew Lawson
(74) *Attorney, Agent, or Firm* — Lerner, David, Littenberg, Krumholz & Mentlik, LLP (57) ABSTRACT

A bone plate mounted on a bone. The bone plate has at least one opening for receiving a flush mounted cam. A through-bore passes from a side surface to opposing side surface of the bone plate. The through-bore has a diameter sized to allow insertion of a cable. A portion of the through-bore intersects with a peripheral portion of the opening. A second opening also passes from the side surface to opposing side surface. A cable may be inserted in the second opening, wrapped around the bone and its free end inserted in the through-bore. The cable may be tightened around the bone. The flush mounted cam can be rotated in place. Rotation of the cam results in the cam surface squeezing the cable between concave cam surface and walls of the opening, thereby locking the cable in the tightened state.

15 Claims, 8 Drawing Sheets

U.S. PATENT DOCUMENTS

| | | | |
|---|---|---|---|
| 5,720,747 A | 2/1998 | Burke | |
| 5,741,259 A | 4/1998 | Chan | |
| 5,810,824 A | 9/1998 | Chan | |
| 5,810,825 A | 9/1998 | Huebner | |
| 5,868,748 A | 2/1999 | Burke | |
| 5,888,221 A | 3/1999 | Gelbard | |
| 5,935,133 A | 8/1999 | Wagner et al. | |
| 5,964,769 A | 10/1999 | Wagner et al. | |
| 5,993,452 A | 11/1999 | Vandewalle | |
| 6,017,347 A | 1/2000 | Huebner et al. | |
| 6,053,921 A | 4/2000 | Wagner et al. | |
| 6,086,590 A * | 7/2000 | Margulies et al. | 606/263 |
| 6,338,734 B1 | 1/2002 | Burke et al. | |
| 6,387,099 B1 | 5/2002 | Lange et al. | |
| 6,391,030 B1 | 5/2002 | Wagner et al. | |
| 6,520,965 B2 | 2/2003 | Chervitz et al. | |
| 6,524,315 B1 | 2/2003 | Selvitelli et al. | |
| 6,682,533 B1 * | 1/2004 | Dinsdale et al. | 606/74 |
| 6,960,213 B2 * | 11/2005 | Chervitz et al. | 606/74 |
| 2003/0187434 A1 * | 10/2003 | Lin | 606/61 |
| 2004/0097942 A1 | 5/2004 | Allen et al. | |
| 2004/0172028 A1 | 9/2004 | Roger | |
| 2005/0171547 A1 * | 8/2005 | Aram | 606/74 |
| 2006/0058795 A1 | 3/2006 | Boyd | |
| 2006/0135958 A1 | 6/2006 | Marissen et al. | |
| 2006/0206114 A1 * | 9/2006 | Ensign et al. | 606/61 |
| 2006/0235401 A1 * | 10/2006 | Baldwin et al. | 606/69 |
| 2006/0276896 A1 * | 12/2006 | Fallin et al. | 623/16.11 |

FOREIGN PATENT DOCUMENTS

| | | |
|---|---|---|
| DE | 9417019 U1 | 1/1995 |
| EP | 0019062 | 11/1980 |
| EP | 0791338 A2 | 8/1997 |
| EP | 0 955 013 A1 | 11/1999 |
| FR | 2614781 A1 | 11/1988 |
| GB | 235167 A | 7/1926 |
| GB | 2311664 | 10/1997 |
| GR | 1003502 B2 | 1/2001 |
| WO | 9303681 A1 | 3/1993 |
| WO | 9318716 A1 | 9/1993 |
| WO | 9428812 A1 | 12/1994 |
| WO | 9522294 A1 | 8/1995 |
| WO | 9835623 A1 | 8/1998 |
| WO | 02067769 A2 | 9/2002 |
| WO | 2004019797 A2 | 3/2004 |
| WO | 2004107996 A1 | 12/2004 |
| WO | 2007047467 A1 | 4/2007 |
| WO | 2008019511 A1 | 2/2008 |

OTHER PUBLICATIONS

AcroMed Publication entitled, "AcroMed Spinal Solutions for Cervical Pathologies," Jul. 1995, pp. 1-8.
Zimmer Cable Ready Brochure.
International Search Report, PCT/EP2008/062913.
Smith & Nephew, Accord Calbe System.
Cable Ready Cable Grip System.

* cited by examiner

CAM-LOCKING OF CABLE FOR FRACTURE PLATE

BACKGROUND OF THE INVENTION

1. Field of Invention

The present invention relates to a cable loop system for use with a bone plate for repairing fractured bones. More particularly the invention relates to a cable loop system that utilizes cam action and is mounted flush with the surface of the bone plate.

2. Description of Related Art

Surgical cables are used in many surgical procedures. Some conventional methods of bone fixation use plates screwed to the bone and cable and crimp system. Other conventional methods have cables and screws that bear upon the cable incorporated in a bone plate. The conventional systems are bulky, hard to work with and require special tools. These systems also have parts that project from the bone plate. There is a need for an easy to use system wherein the cable loop is easy to install, does not require special tools and does not project beyond the surface of the bone plate.

SUMMARY OF THE INVENTION

The present invention includes a bone plate mounted on a bone. The bone plate has at least one opening for receiving a flush mounted cam. A through-bore passes from a side surface to opposing side surface of the bone plate. The through-bore has a diameter sized to allow insertion of a cable. A portion of the through-bore intersects with a peripheral portion of the opening. A second through-bore also passes from the side surface to opposing side surface. The second through-bore has stepped construction.

A cable may be inserted in the second through-bore, wrapped around the bone and its free end inserted in the through-bore resulting in cable being wrapped around the bone. The cable may be tightened and locked in the tightened state.

A flush mounted cam has a cam surface between upper surface and lower surface. Substantial portion of the cam surface has a concave profile. Flush mounted cam can be rotated in place by inserting a screwdriver in the screwdriver slot on the upper surface In use, the bone plate is attached to fractured bone. Next, cable is inserted in through-bores and wrapped around bone using techniques known to one skilled in the art. With the cable pulled tight around bone, flush mounted cam is rotated in the opening. Rotation of the cam results in the cam surface squeezing the cable between concave cam surface and walls of the opening, thereby locking the cable in the tightened state.

DETAILED DESCRIPTION

Figure 1:
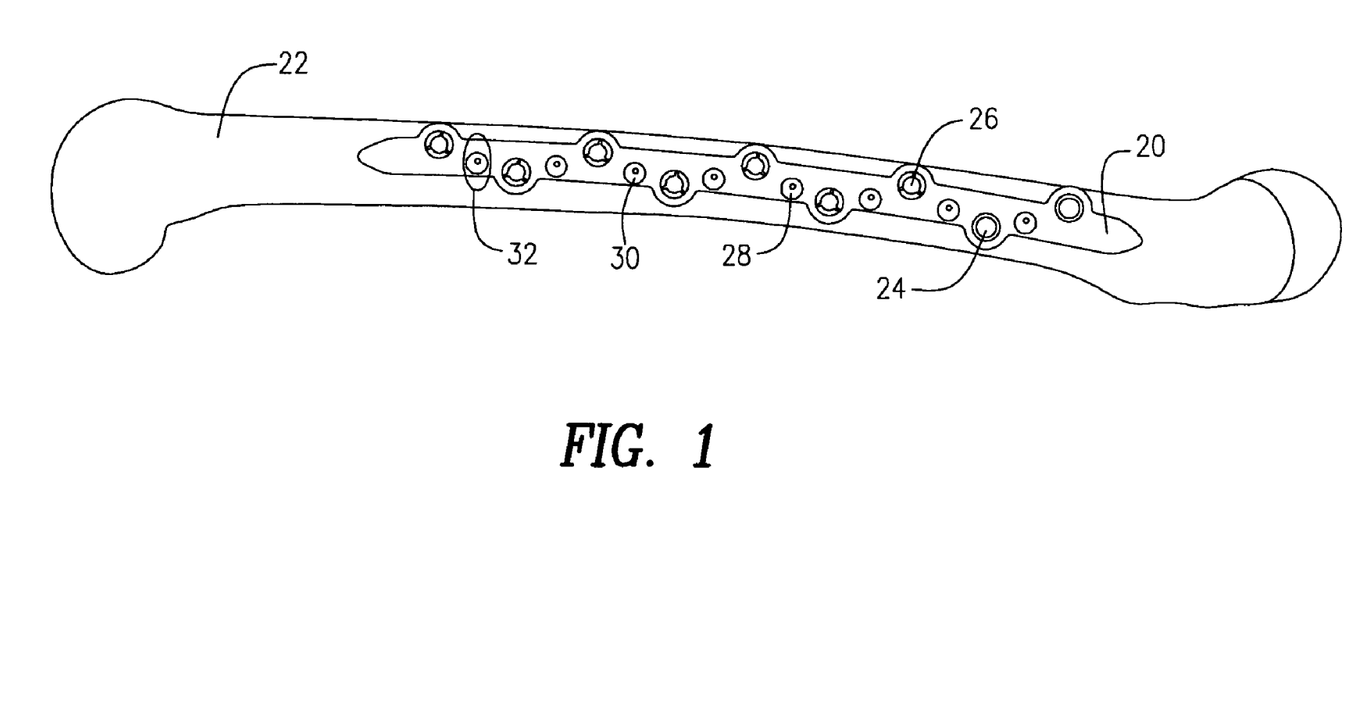
FIG. 1 shows a bone plate with flush mounted cams mounted on a bone.
Figure 2A:
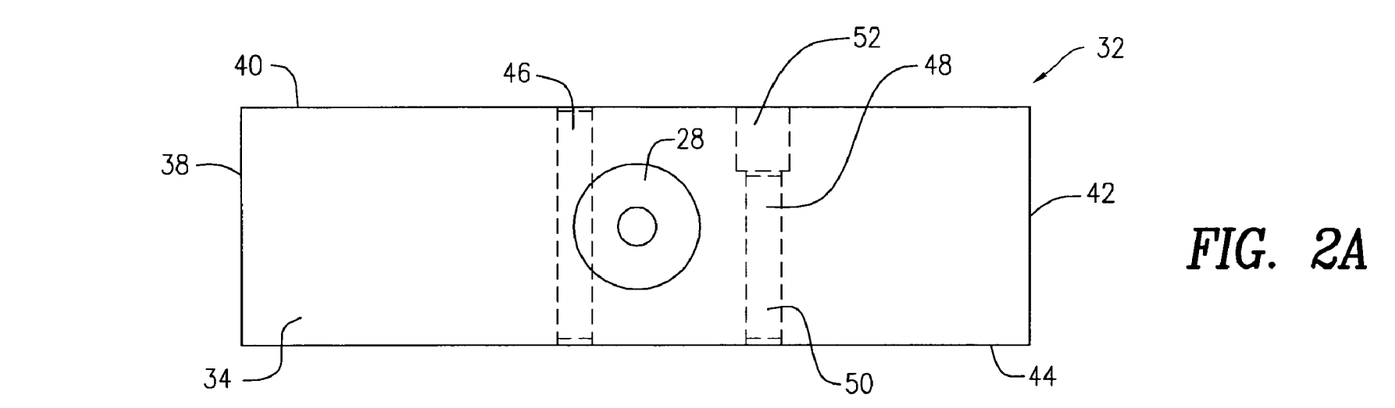
FIG. 2A is a plan view of a section of the bone plate of FIG. 1.
Figure 2B:
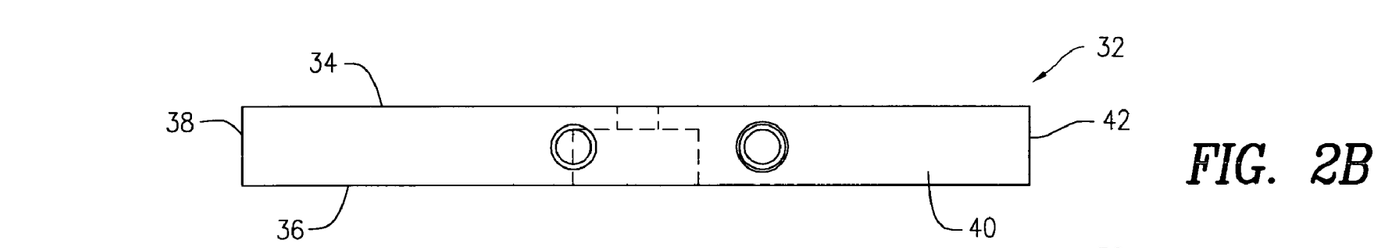
FIG. 2B is a side view of the section shown in FIG. 2A.
Figure 2C:
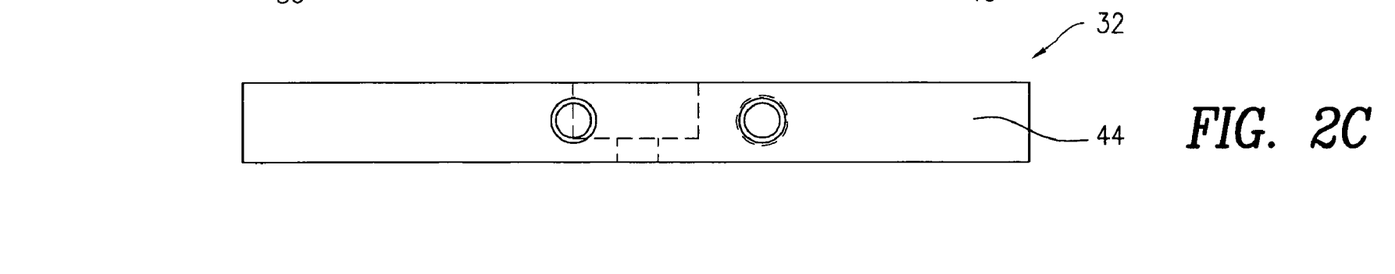
FIG. 2C is another side view of the section shown in FIG. 2A.

FIG. 1 shows a bone plate 20 mounted on a bone 22. Bone plate 20 has openings 24 for receiving screws 26. Screws 26 are inserted in openings 24 and screwed in bone 22 to attach bone plate 20 to bone 22. Bone plate 20 also has openings 28 (FIG. 5A) for receiving a flush mounted cam 30. FIGS. 2A, 2B and 2C show a segment 32 of bone plate 20 having one opening 28 for receiving flush mounted cam 30. Bone plate 20 may include a plurality of segments 32 depending upon the size of bone plate 20. Segment 32 has a top surface 34 a bottom surface 36 and four side surfaces 38, 40, 42 and 44. Side surfaces 38 and 42 are integral with the body of bone plate 20. A through-bore 46 passes from side surface 40 to side surface 44. Through-bore 46 has a diameter sized to allow insertion of a cable. A portion of through-bore 46 intersects with a peripheral portion of opening 28. A second through-bore 48 also passes from side surface 40 to side surface 44. Second through-bore 48 has stepped construction. A first portion 50 of second through-bore 48 has same diameter as through-bore 46, whereas a second portion 52 has a larger diameter.

Figure 3:
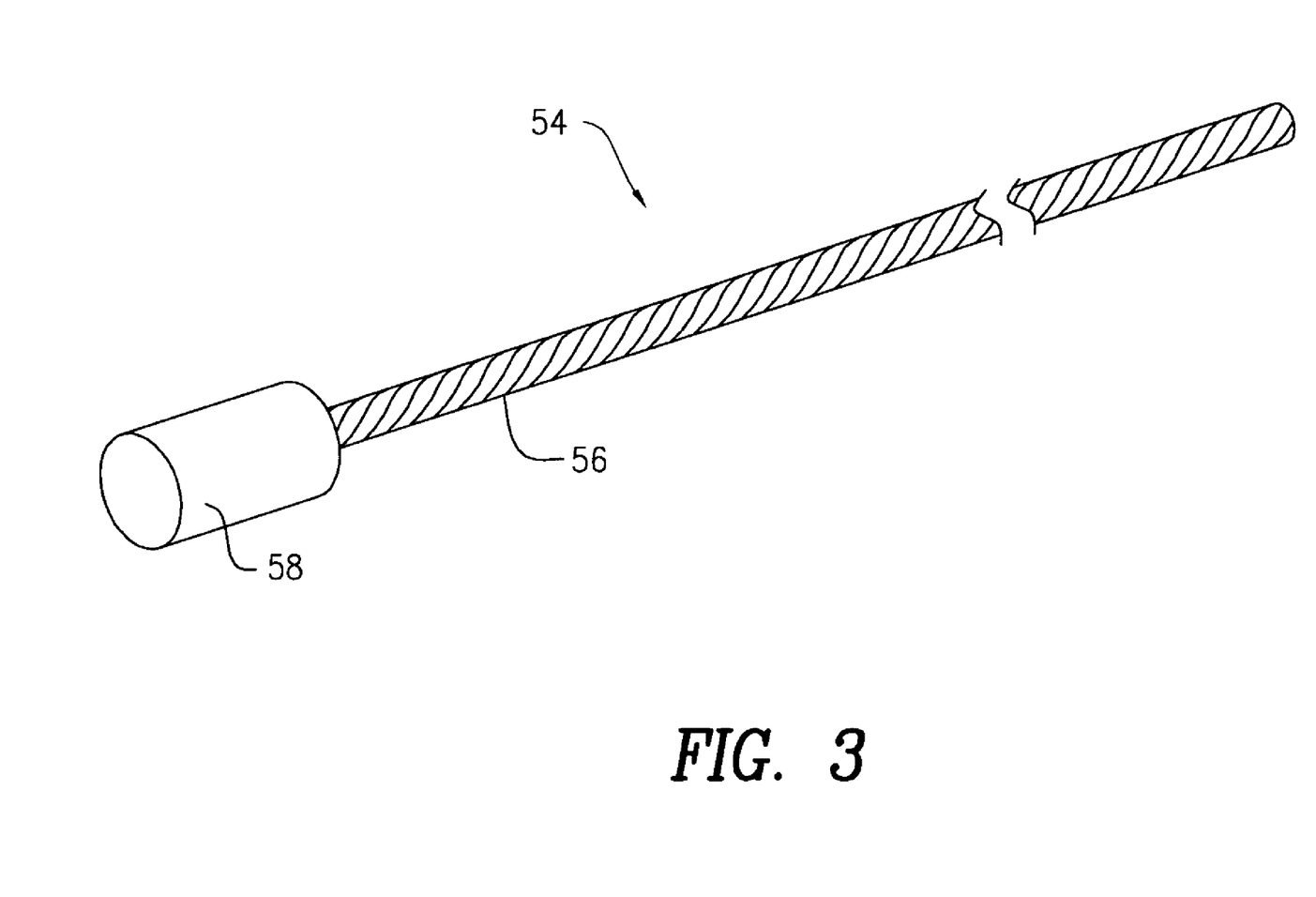
FIG. 3 shows a cable for used with the bone plate of FIG. 1.

A cable 54 (FIG. 3) has a body 56 and a first end 58 that has a larger diameter than body 56. The diameter of the first end 58 is such that it slides in second portion 52 of through-bore 48 but is too large to enter first portion 50 of through-bore 48. Cable 54 may be inserted in through bore 48, wrapped around bone 22 and its free end inserted in through-bore 46 resulting in cable 54 being wrapped around bone 22. Cable 54 may be tightened and locked in the tightened state as described hereafter. Cable 54 may be made of any suitable biocompatible material including various polymers and metals. Cable 54 may be made from strands of one or more materials.

Figure 4A:
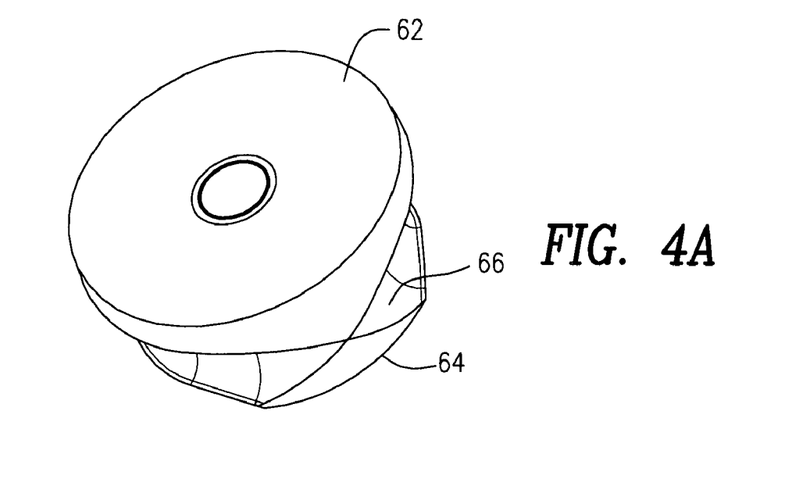
FIG. 4A is an isometric view of a flush mounted cam for use with the bone plate of FIG. 1.
Figures 4B, 4C:
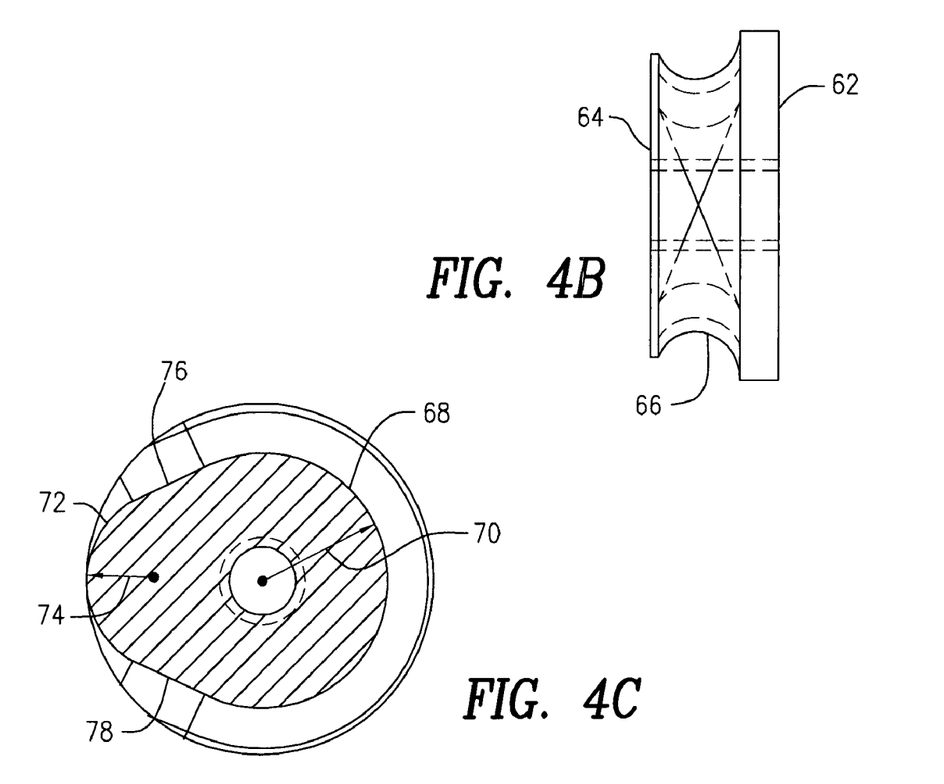
FIG. 4B is a side view of the flush mounted cam of FIG. 4A.
FIG. 4C is a sectional view of the flush mounted cam of FIG. 4A.

FIGS. 4A, 4B, and 4C show flush mounted cam 30. Cam 30 has an upper surface 62 a lower surface 64 and a cam surface 66 between upper surface 62 and lower surface 64. FIG. 4C is a cross-section taken through approximately middle of cam surface 66. As seen in FIG. 4C, the periphery of cam surface 66 has a first section 68 having a first radius 70 that may be of constant magnitude. The periphery of cam surface 66 has a second section 72 that has a second radius 74. In another embodiment, the periphery of cam surface 66 may be curved with the curve having a variable radius. The second radius 74 may be larger or smaller than the first radius 70. First section 68 and second section 72 are connected with each other via sections 76 and 78. The outer periphery of cross-section seen in FIG. 4C is constituted by first section 68, second section 72, section 76 and section 78 and forms a portion of cam surface 66. Substantial portion of cam surface 66 has concave profile as seen in FIG. 4B. A hole 82 is located in the center of flush mounted cam 30. Hole 82 may be threaded. A screwdriver slot 83 (FIG. 5B) may be formed on upper surface 62. Flush mounted cam 30 is inserted in opening 28. Flush mounted cam is captured in opening 28 such that it can be rotated in place by inserting a screwdriver in the screwdriver slot on upper surface 62. When flush mounted cam 30 is inserted in opening 28, no part of cam 30 protrudes above the surface of the bone plate.

Figure 5A:
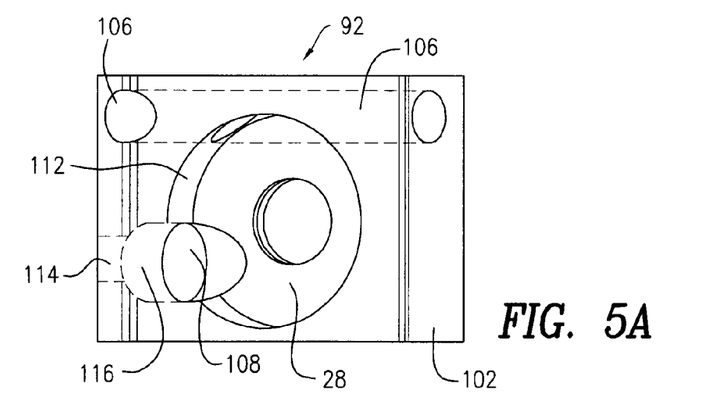
FIG. 5A shows an isometric view of a section of an alternative embodiment of the bone plate of FIG. 1.
Figure 5B:
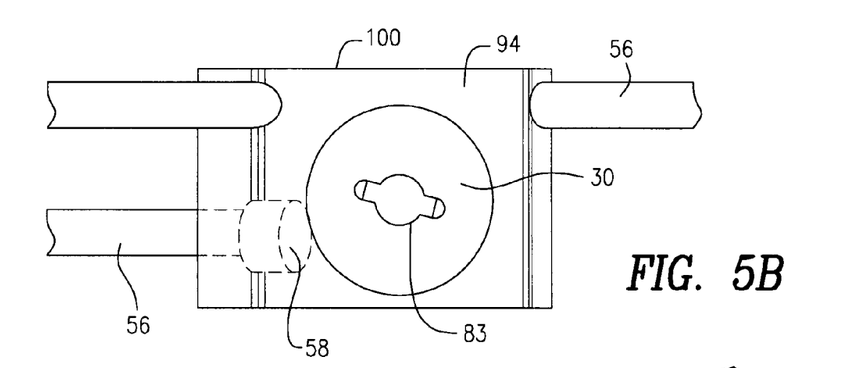
FIG. 5B is a top view of the section shown in FIG. 5A with the flush mounted cam installed therein.
Figure 5C:
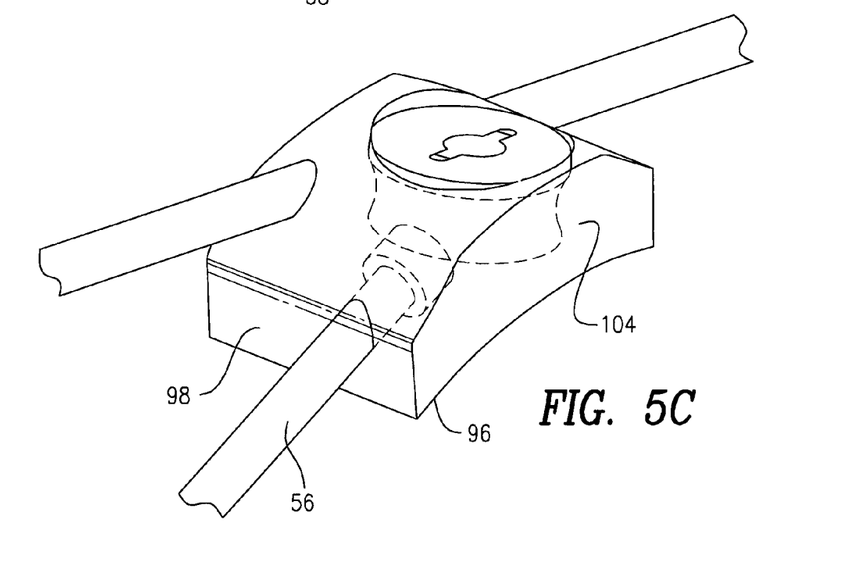
FIG. 5C is another isometric view of a section of an alternative embodiment of the bone plate of FIG. 1 with the flush mounted cam installed therein.

FIGS. 5A, 5B and 5C show a segment 92 of another embodiment of bone plate 20. Segment 92 has one opening 28 for receiving flush mounted cam 30. Segment 92 has a top surface 94, a bottom surface 96 and four side surfaces 98, 100, 102 and 104. A bore 106 passes from side surface 102 to top surface 94. Bore 106 has a diameter sized to allow insertion of cable body 56. A portion of through-bore 106 intersects with a peripheral portion of opening 28. A second bore 108 passes from internal surface 112 of opening 28 to side surface 98. Second bore 108 has stepped construction. A first portion 114 of second bore 108 has same diameter as bore 106, whereas a second portion 116 has a larger diameter. First end 58 of cable 54 may slide in second portion 116 of second bore 108 but is too large to enter first portion 114 of second bore 108.

In use, bone plate 20 is attached to fractured bone 22 by inserting in bone 22 one or more screws 26 through openings 24. The number of screws 26 can vary depending upon the size of bone plate 20. Next, cable 54 is inserted in throughbore 48 (or second bore 108) and pulled tight so that first end 58 of cable 54 bottoms in second portion 52 (or second portion 116) and cannot move any further. Next, cable 54 is wrapped around bone 22 using techniques known to one skilled in the art. Free end of cable 54 is passed through through-hole 46 (or bore 106) and pulled tight against the bottomed first end 58. Cable 54 is pulled tight using one of the techniques known to one skilled in art. With cable 54 pulled tight around bone 22, flush mounted cam 30 is rotated in opening 28. Rotation of cam 30 results in the cam surface squeezing cable 54 between concave cam surface 66 and walls of opening 28, thereby locking cable 54 in the tightened state. To loosen cable 54, flush mounted cam 30 is rotated in opposing direction, thereby eliminating the squeezing action and allowing cable 54 to be loosened.

Figure 6A:
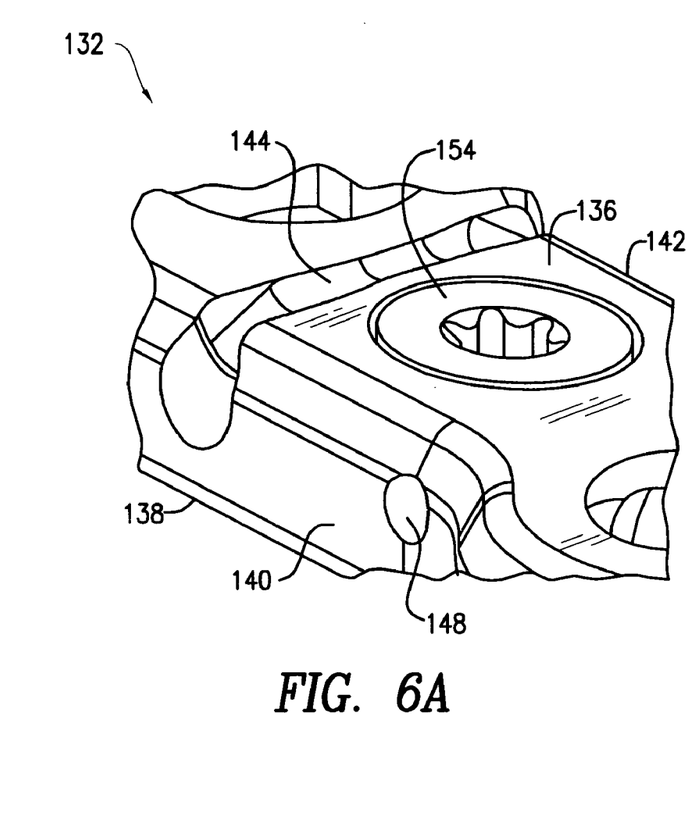
FIG. 6A shows an isometric view of a section of an alternative embodiment of the bone plate of FIG. 1.
Figure 6B:
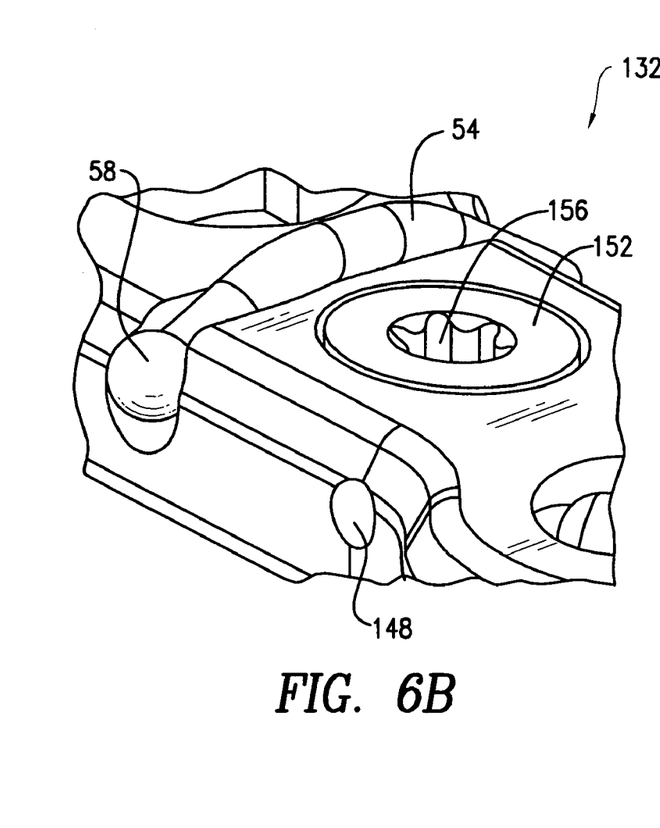
FIG. 6B shows an isometric view of a section of an alternative embodiment of the bone plate of FIG. 1 with cable of FIG. 3 installed therein.
Figure 6C:
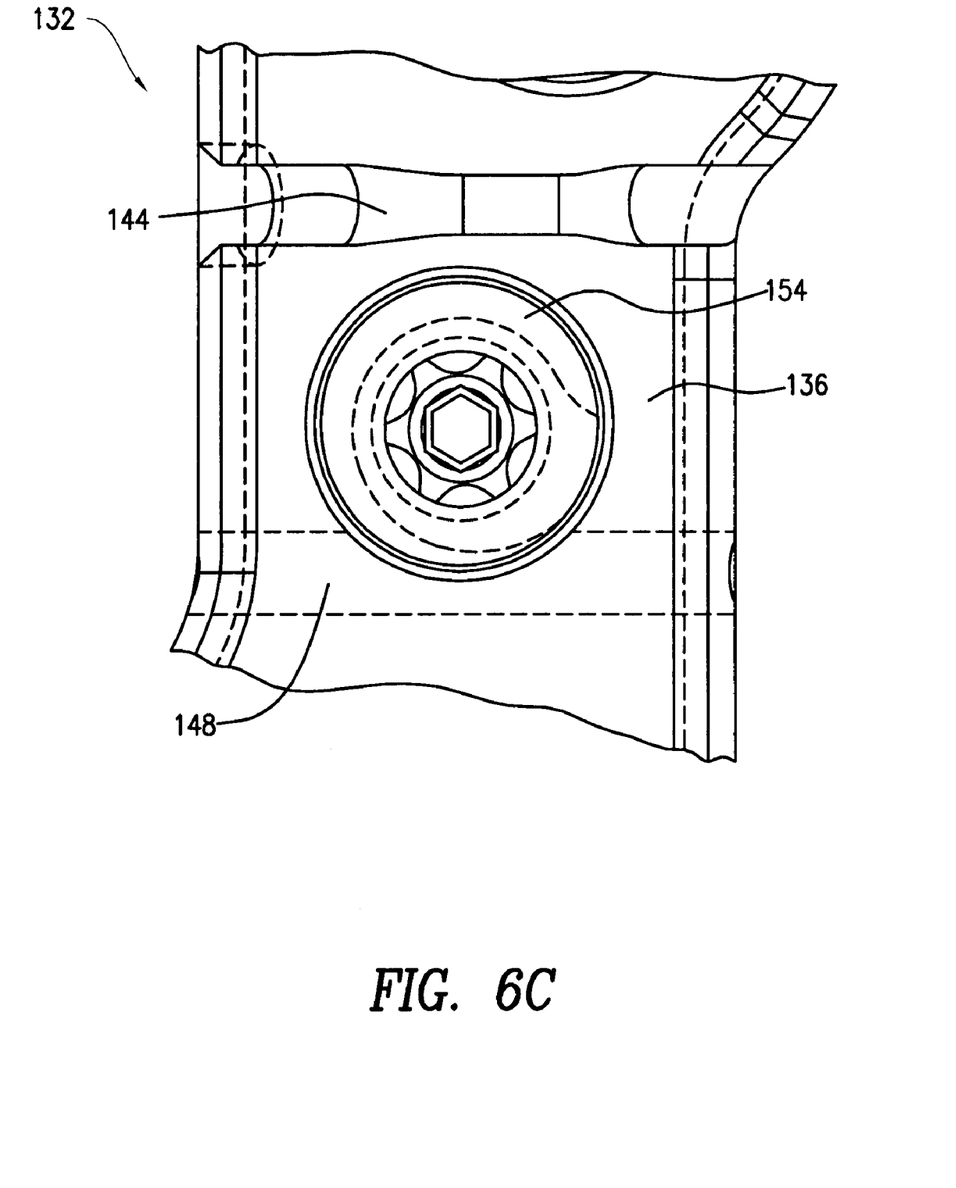
FIG. 6C is a plan view of a section of an alternative embodiment of the bone plate of FIG. 1.
Figure 7A:
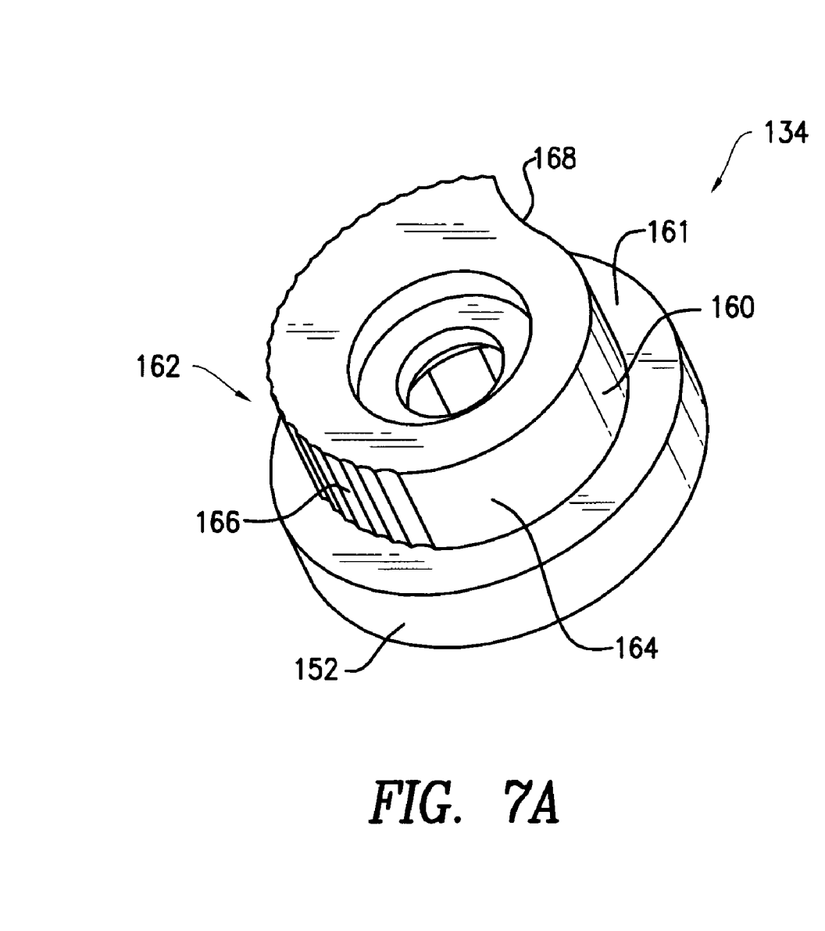
FIG. 7A shows an isometric view of another embodiment of a flush mounted cam for use with the bone plate of FIG. 1.
Figure 7B:
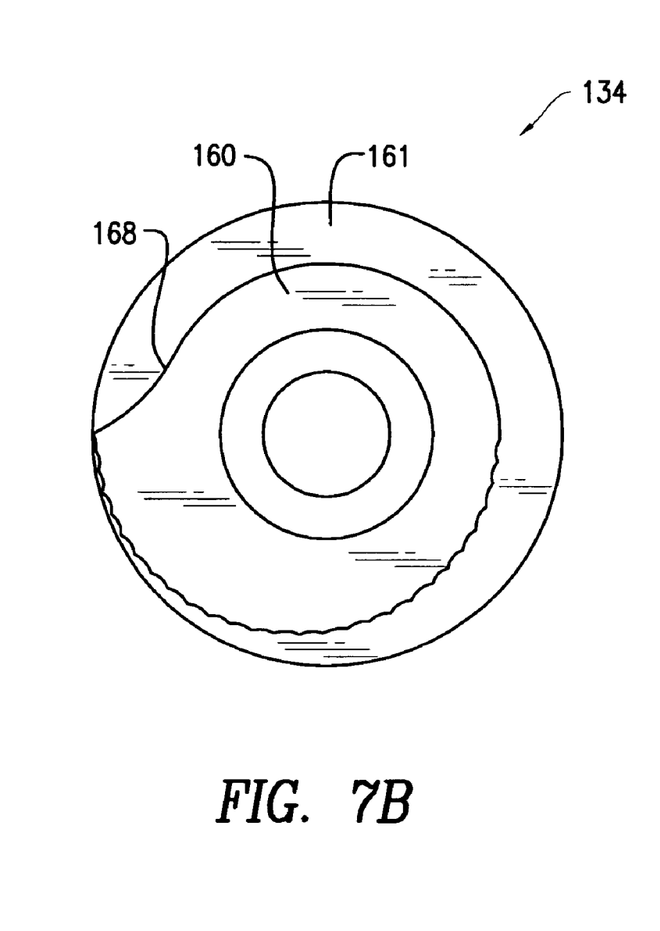
FIG. 7B is a plan view of the flush mounted cam of FIG. 7A.

FIGS. 6A, 6B and 6C show a segment 132 of yet another embodiment of bone plate 20. Segment 132 has one opening 28 for receiving flush mounted cam 30 or alternately receiving flush mounted cam 134 (FIGS. 7A and 7B). Segment 132 has a top surface 136, a bottom surface 138, a front side surface 140 and a back side surface 142. A groove 144 extends from side surface 140 to side surface 142. Groove 144 is open and therefore accessible at top surface 136. Groove 144 extends from top surface 136 towards bottom surface 138 but does not reach bottom surface 138. Groove 144 has a larger diameter at its end that is close to side surface 140. Alternatively, the larger diameter may be at the opposing end. Groove 144 may have different diameter for sections along it length. The diameter of a section along its length may be adapted to allow insertion of cable body 56 in groove 144. A bore 148 extends from side surface 140 to side surface 142. Bore 148 has a diameter sized to allow insertion of cable 56. A portion of bore 148 intersects with a peripheral portion of opening 28.

Cam 134 is an alternative embodiment of cam 30 that may be inserted in opening 28. Cam 134 and cam 30 may be used alternatively with any embodiment of bone plate 20. Cam 134 has a top portion 152 (FIG. 7A) that may be circular. Top surface 154 of top portion 152 has a screw driver slot 156 formed therein. A bottom portion 160 is connected to a bottom surface 161 of top portion 152. Bottom portion 160 is smaller than top portion 152, thus, a shoulder is formed at the junction of top portion 152 and bottom portion 160. Bottom portion 160 has generally arcuate surface 162. Arcuate surface 162 has a first section 164 that has a first diameter. The surface of the first section 164 blends into the surface of a second section 166 and the surface of a third section 168. Second section 166 has a second diameter that is larger then the first diameter. The surface of third section 168 blends on one end with the surface of first section 164 and at the opposing end with the surface of second section 166. The surfaces of first section 164, second section 166 and third section 168 form a continuous cam surface. The cam surface is such that when cam 134 is installed in opening 28 in a first position the distance between the cam surface and the opposing surface of bore 148 is larger than the distance between them when cam 134 is rotated to a second position. To enhance the gripping of cable body 56 in the bone plate 20, at least a portion of the surface of second section 166 may be made rough by use of techniques known to one skilled in the art.

In use, bone plate 20 is attached to fractured bone 22 by inserting in bone 22 one or more screws 26 through openings 24. The number of screws 26 can vary depending upon the size of bone plate 20. Next, cable 54 is inserted in groove 144 and pulled tight so that first end 58 of cable 54 is in the larger diameter portion of groove 144 and cannot move any further along groove 144. Since groove 144 is accessible from top surface 154, it is not necessary to thread cable 54 through a hole. Next, cable 54 is wrapped around bone 22 using techniques known to one skilled in the art. Free end of cable 54 is passed through bore 148 and pulled tight against the bottomed first end 58. Cable 54 is pulled tight using one of the techniques known to one skilled in art. With cable 54 pulled tight around bone 22, flush mounted cam 134 is rotated in opening 28. Rotation of cam 30 results in the cam surface that is rough squeezing cable 54 against the wall of opening 28, thereby locking cable 54 in the tightened state. The rough surface finish on the surface of cam 134 ensures a tight grip that prevents the cable from slipping and getting loose. To loosen cable 54, flush mounted cam 134 is rotated in opposing direction, thereby eliminating the squeezing action and allowing cable 54 to be loosened.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A cam-locking system comprising: a body having a top elongate planar surface and first and second bores, the first and second bores extending across the body and being substantially parallel to one another and a recess formed in the body and communicating with at least one of the first and second bores;

a cable, the cable passing through the first and second bores and adapted to be pulled tight; and a flush mounted cam, the cam having a top surface, a bottom surface, and a cam surface between the top and bottom surfaces, the cam being inserted in the recess such that when the cam is fully seated in the recess the top surface of the cam and the top elongate planar surface of the body form an uninterrupted flat surface, the cam being operable between a first position that allows the cable to be tightened and a second position that locks the cable in the tightened state, wherein the cam surface only comes in contact with the cable in either the first or second bores, and defines a plane along a width thereof, and the cam surface further comprises;

a first portion having a first radius; and a second portion having a second radius, wherein the first portion and the second portion are disposed along the plane of the cam surfaces.

2. The cam-locking system of claim 1, wherein the cable further comprises:

a first end;

a second end, and a length extending between the first end and the second end, the length having a first diameter, and wherein the diameter of the first end or the second end is larger than the first diameter.

3. The cam-locking system of claim 2, wherein the cable is made from a material selected from a group consisting of biocompatible materials, metal and strands of biocompatible material.

4. The cam-locking system of claim 1, wherein the second radius is larger than the first radius.

5. The cam-locking system of claim 4, wherein the profile of the cam surface is concave.

6. The cam-locking system of claim 5, wherein at least a portion of the cam surface has rough texture.

7. A bone plate system comprising: a plate having a top elongate planar surface; at least one screw hole adapted to receive a screw for mounting the plate on a bone;

first and second bores formed in the plate, the first bore and second bore each extending across the plate and being substantially parallel to one another, the plate having a recess communicating with only one of the first and second bores;

a cable, the cable passing through the first and second bores and adapted to be pulled tight; and a flush mounted cam, the cam having a top surface, a bottom surface, and a cam surface between the top and bottom surfaces, the cam configured to be retained entirely within the recess such that when the cam is fully seated in the recess the top surface of the cam and the top elongate planar surface of the body form an uninterrupted flat surface, the cam being operable between a first position that allows the cable to be tightened and a second position that locks the cable in the tightened state, wherein the cam surface defines a plane along a width thereof, and the cam surface further comprises:

a first portion having a first radius;

a second portion having a second radius;

wherein the first portion and the second portion are disposed along the plane of the cam surface.

8. The bone plate system of claim 7, wherein the cable further comprises:

a first end;

a second end, and a length extending between the first end and the second end, the length having a first diameter, and wherein the diameter of the first end or the second end is larger than the first diameter.

9. The bone plate system of claim 8, wherein the cable is made from a material selected from a group consisting of biocompatible materials, metal and strands of biocompatible material.

10. The bone plate system of claim 7, wherein the second radius is larger than the first radius.

11. The bone plate system of claim 10, wherein the profile of the cam surface is concave.

12. The bone plate system of claim 11, wherein at least a portion of the cam surface has rough texture.

13. The bone plate system of claim 7, wherein at least a portion of the cam surface has rough texture.

14. A cam-locking system comprising: a body having a top elongate planar surface and first and second bores, the first and second bores extending across the body and being substantially parallel to one another and a recess formed in the body and communicating with at least one of the first and second bores;

a cable, the cable passing through the first and second bores and adapted to be pulled tight; and a flush mounted cam, the cam having a top portion and a bottom portion connected to the top portion, the bottom portion having a side cam surface, the cam being inserted in the recess such that when the cam is fully seated in the recess the top portion of the cam and the top elongate planar surface of the body form an uninterrupted flat surface, the cam being operable between a first position that allows the cable to be tightened and a second position that locks the cable in the tightened state, wherein the side cam surface of the bottom portion of the cam only comes in contact with the cable in either the first or second bores, wherein the side cam surface defines a plane along a width thereof, and the cam surface further comprises;

a first portion having a first radius;

a second surface portion having a second radius;

wherein the first portion and the second portion are disposed along the plane of the cam surface.

15. The cam-locking system of claim 14, wherein at least a portion of the side cam surface has a rough texture.

* * * * *